United States Patent [19]

Mane et al.

[11] Patent Number: 5,843,466
[45] Date of Patent: *Dec. 1, 1998

[54] COOLANT COMPOSITIONS

[75] Inventors: Jean M. Mane; Jean-Louis Ponge, both of Grasse, France

[73] Assignee: V. Mane Fils S.A., France

[ * ] Notice: The term of this patent shall not extend beyond the expiration date of Pat. No. 5,725,865.

[21] Appl. No.: 629,598

[22] Filed: Apr. 9, 1996

Related U.S. Application Data

[63] Continuation-in-part of Ser. No. 520,399, Aug. 29, 1995, Pat. No. 5,725,865.

[51] Int. Cl.$^6$ .............................. A61K 9/14; A61K 9/20; A61K 9/68
[52] U.S. Cl. ............................................ 424/401
[58] Field of Search ............................ 424/48, 439, 440, 424/441, 442, 49, 401, 65, 69, 70.1, 73, 464, 489, 400, 55

[56] References Cited

U.S. PATENT DOCUMENTS

| | | | |
|---|---|---|---|
| 3,111,127 | 11/1963 | Jarboe | 131/17 |
| 4,157,384 | 6/1979 | Watson et al. | 424/45 |
| 5,009,893 | 4/1991 | Cherukuri et al. | 424/440 |

FOREIGN PATENT DOCUMENTS

| | | |
|---|---|---|
| 2339661 | 8/1973 | Germany. |
| 2608226 | 9/1977 | Germany. |
| WO/9323005 | 11/1993 | WIPO. |
| WO 93/25177 | 12/1993 | WIPO. |

OTHER PUBLICATIONS

"A Molecular Approach to Flavor Synthesis. I. Menthol Esters of Varying Size and Polarity", by Jabloner et al, Hercules Incorporated Research Center, Wilimgton, Delaware, 1989.

*Primary Examiner*—Thurman K. Page
*Assistant Examiner*—James M. Spear
*Attorney, Agent, or Firm*—Larson & Taylor

[57] ABSTRACT

Coolant compositions, flavorant compositions and ingestible and topical compositions containing at least one coolant compound selected from monomenthyl succinate, alkali metal salts of monomenthyl succinate, alkaline earth metal salts of monomenthyl succinate and mixtures thereof. These compositions are found to provide a pleasant, long-lasting cooling effect without bitterness and the cooling effect manifests itself differently than the cooling effect of other known coolants. As a result, a complementary or synergistic effect can by obtained by combination with other coolants. Further, the succinate-based coolant compounds of the invention are found to enhance the sensation of alcohol in alcoholic beverages.

18 Claims, No Drawings

COOLANT COMPOSITIONS

BACKGROUND OF THE INVENTION

1. Related Applications

This application is a continuation-in-part of U.S. application Ser. No. 08/520,399 filed on Aug. 29, 1995 U.S. Pat. No. 5,725,865.

2. Field of the Invention

This invention relates to coolant compositions having a unique cooling perception that provides the user with a pleasing cooling effect without bitterness. The invention also relates to products containing one or more coolant compounds.

3. Description of the Prior Art

A variety of compounds are known which provide a cooling sensation when ingested or contacted with the body. Perhaps the best known of these compounds is menthol. It is believed that menthol acts on the cold receptors at the nerve endings in order to provide this cooling effect.

Since menthol has a strong minty odor and high relative volatility, several other coolant compounds have been developed and reported in the technical literature as potential flavorants or odorants in a variety of topical and ingestible compositions. For example, U.S. Pat. No. 5,009,893 proposes the use of menthol in combination with N-substituted-p-menthane carboxamide compounds as coolant compositions in edible products.

International Patent application publication No. WO93/23005 proposes coolant compositions for edible or topical products which comprise a ketal and a secondary coolant which may be selected from menthol, carboxamides and mixtures thereof. In addition, this patent application mentions several other references which disclose compounds which have a flavor resembling menthol including menthyl carbinol, saccharide esters of menthol and a variety of amides. Also mentioned is that 2,3-p-menthane diol has been reported as having a sharp cooling taste.

German Patent application 2 339 661 discloses aromatic compositions which include menthol or menthol esters of heterocyclic carboxylic acids. The preferred ester is menthyl-2-pyrrolidone-5-carboxylic acid ester.

German Patent application 26 08 226 discloses a composition which exhibits a physiological cooling effect. The cooling compounds disclosed include menthol esters of naturally occurring hydroxycarboxylic acids having 2–6 carbon atoms which are esterified with a $C_1$–$C_4$ alkyl group. Menthyl acetate and menthyl lactate are the most preferred cooling compounds of this disclosure. Finally, another commercially available coolant compound is 3-menthoxypropane-1,2 diol.

Thus, a variety of compounds are known which provide cooling properties and are useful in a wide variety of products. However, there is still a need to provide coolant compositions having an improved cooling effect and/or taste perception.

Accordingly, it is an object of the present invention to provide improved coolant compositions.

It is a further object of the present invention to provide coolant compositions having a unique cooling sensation and taste perception.

It is a still further object of the present invention to provide coolant compositions including two or more cooling agents which provide a complementary cooling sensation and taste perception.

It is a still further object of the present invention to provide a novel coolant composition which employs a non-toxic coolant having a unique cooling sensation and taste perception.

These and other objects of the present invention will be apparent from the description which follows.

SUMMARY OF THE INVENTION

The present invention relates to a composition selected from topical products, oral care products, nasal care products, toilet articles, ingestible products and chewing gum, which comprises a product base and an effective amount of a cooling compound selected from monomenthyl succinate, alkali metal salts of monomenthyl succinate and alkaline earth metal salts of monomenthyl succinate.

In a second aspect, the present invention relates to a composition including a coolant selected from monomenthyl succinate, alkali metal salts of monomenthyl succinate and alkaline earth metal salts of monomenthyl succinate formulated with a diluent selected from the group of flavors, flavoring oils and herbal oils.

The present invention also relates to coolant compositions which include a primary coolant selected from monomenthyl succinate, alkali metal salts of monomenthyl succinate and alkaline earth metal salts of monomenthyl succinate, and at least one secondary coolant component.

Monomenthyl succinate is a known compound having Chemical Abstracts no. 77341-67-4. It has been used, for example, in smoking tobacco products as is disclosed in U.S. Pat. No. 3,111,127. In particular, this patent discloses spraying monomenthyl succinate onto tobacco products which were then fabricated into cigarettes. These tobacco products were evaluated and observed to burn slower at smolder than a comparable control product, to have increased firmness, and to require more puffs under a controlled smoking regime. Further, when tested organoleptically, these products were found to deliver smoke having the pleasing and cooling taste and aroma characteristic of menthol.

The article, "A Molecular Approach to Flavor Synthesis. I. Menthol Esters of Varying Size and Polarity," Jabloner, H. and Dunbar, B. I., *J. of Polymer Science,* Vol. 18, pages 2933–40 (1980) discloses a method for the synthesis of monomenthyl succinate as well as monomenthyl sodium succinate and other menthol esters derived from monomenthyl succinate. Solutions of 5% by weight of several of these menthol esters in mineral oil or water were tasted by a nine person taste panel. 5% of dimenthyl succinate in mineral oil was found to be odorless and tasteless, 5% sodium monomenthyl succinate in water was found to be vile and bitter and monomenthyl succinate itself was not tasted.

The present inventors have surprisingly found that monomenthyl succinate, alkali metal salts of monomenthyl succinate and alkaline earth metal salts of monomenthyl succinate used in a variety of ingestible and topical products at low concentrations of up to 1% by weight, give a pleasing, long-lasting cooling effect rather than the vile and bitter taste observed by the taste panel in the Jabloner article.

DETAILED DESCRIPTION OF THE PREFERRED EMBODIMENTS

The present invention relates to an end use composition selected from topical products, oral care products, nasal care products, toilet articles, ingestible products and chewing gum, which comprises a product base and an effective amount of a cooling compound selected from monomenthyl succinate, alkali metal salts of monomenthyl succinate and alkaline earth metal salts of monomenthyl succinate (hereinafter collectively referred to as "succinate-based coolant compounds"). More preferably, the coolant employed in the compositions of the present invention is selected from monomenthyl succinate, monomenthyl sodium succinate, monomenthyl potassium succinate, monomenthyl lithium succinate, monomenthyl calcium succinate, monomenthyl magnesium succinate and monomenthyl barium succinate, as well as mixtures thereof.

It has been surprisingly found that these succinate-based coolant compounds, when used in low concentrations of up to 1% by weight based on the total weight of the end use composition into which they are incorporated, provide a pleasing cooling, or long-lasting cooling effect without the bitterness which would be expected from the prior art. Further, at concentrations of up to 1% by weight, the succinate-based coolant compounds do not develop a strong minty taste in the mouth or throat as do other coolants such as menthol.

The present inventors have also found that the succinate-based coolant compounds of the present invention provide a cooling effect in a different area of the mouth and throat when ingested than, for example, menthol or carboxamide-based coolant compounds. As a result, the succinate-based coolants of the present invention provide a complementary or synergistic cooling effect when combined with at least one secondary coolant compound.

The present inventors have also found that the succinate-based coolant compounds of the present invention enhance the taste sensation of alcohol in alcoholic beverages. As a result, alcoholic beverages comprising the succinate-based coolant compounds of the present invention taste like they have a higher alcohol content than equally strong alcoholic beverages without the succinate-based coolant compound.

The choice of the succinate-based coolant compound for use in the coolant composition will depend, to some extent, on the solubility characteristics which are desired of the compound. For example, monomenthyl succinate is sparingly soluble in water and more soluble in oil. Thus, monomenthyl succinate is particularly suitable for environments where oil solubility is advantageous, although monomenthyl succinate can be used in aqueous environments if a concentration below the water solubility limit is employed. The alkali metal and alkaline earth metal salts of monomenthyl succinate are substantially more soluble in water and, as a result, are most useful in products where water solubility is advantageous.

The end use compositions in which the succinate-based coolant compounds may be employed include a wide variety of ingestible compositions and topical compositions for application to the human or animal body. Ingestible compositions include foodstuffs for human or animal consumption, beverages and other orally ingested compositions for humans or animals such as medicaments, antacids, laxatives, as well as chewing gum compositions. Topical compositions include a wide variety of compositions for application to humans or animals such as toiletries, oral care products, nasal care products, lotions, oils and ointments which are applied to the human body.

In formulating the compositions of the present invention, the coolant compound can be employed in the form of a coolant composition, a flavoring composition and/or the coolant compound, composition or flavoring composition may be incorporated into a carrier material which may be inert or contain other active ingredients of the end use composition. A wide variety of carrier materials can be employed including, for example, polar solvents, oils, fats, finely divided solids, maltodextrins, cyclodextrins, gums, natural or synthetic resins and any other known carrier materials for coolant or flavoring compositions.

Ingestible compositions in accordance with the present invention include, but are not limited to, alcoholic and non-alcoholic beverages, confectionery compositions including confectionery tablets, hard-boiled candies, chewing gums, pectin-based candies, chewy candies, cream-centered candies and fondants; carbonated beverages, powdered beverage mixes, distilled beverages, mineral waters, baked goods, dairy products, fruit ices, jams, jellies, gelatins, puddings and animal feeds.

Another type of ingestible composition in accordance with the present invention is sugarless candies. Sugarless candies typically have higher boiling points than the corresponding candies including sugar and thus any flavors added thereto must be stable at higher temperatures in order to be successfully added to the sugarless candy. Sugarless candies may include hard-boiled candies, pectin-based candies, chewy candies and cream-centered candies. In addition, sugarless chewing gums may also be made in accordance with the present invention. The amount of cooling composition incorporating in sugarless candies and/or sugarless gums is the same as would be used for the corresponding candies and/or gums including sugar.

The topical compositions of the present invention include, but are not limited to, toiletries such as face creams, talcum powders, hair oils, shampoos, bath oils and salts, toilet soaps, cologne, antiperspirants, toilet water, perfume, shaving lotions and creams, soaps, creams, dentifrices, mouthwashes, hair tonics and other similar products.

The succinate-based coolant of the present invention may also be incorporated into ingestible or topical medicaments such as cough drops, antacids, lozenges, anti-irritants, ointments, lotions, oral analgesics and other similar products. Further, other compositions such as adhesives for a variety of uses where taste perception is a concern can incorporate the cooling and flavorant compositions of the present invention.

The most preferred compositions which will incorporate the succinate-based coolant of the present invention are pressed confectionery tablets, hard-boiled candies, chewing gums, chewy candies, pectin candies, cream-centered candies, fondant, toothpastes, mouthwashes, breath fresheners, alcoholic and non-alcoholic beverages, carbonated beverages and dry beverage mixes.

The amount of coolant composition incorporated in each of these end use compositions will vary depending upon the particular compound, the degree of cooling effect desired and the strength of other flavorants in the composition. Typically, the succinate-based coolant compound will make up from 0.001–1.0% by weight of the end use composition. More preferably, the succinate-based coolant compound makes up 0.005–0.5% by weight, based on the total weight of the end use composition.

In a second aspect, the present invention relates to a flavoring composition including a succinate-based coolant and a diluent selected from flavorants. This composition is particularly useful as a flavoring composition in a variety of ingestible compositions and/or compositions destined for contact with the human or animal body.

The flavorants may be selected from fruit flavors such as strawberry flavor, herbal oils such as eucalyptus oil, peppermint oil, spearmint oil, as well as other known flavors or flavoring oils which are conventionally employed in ingestible compositions and compositions designed for contact with human or animal bodies including flavors such as flavoring syrups such as sorbitol syrup or other sweetening or flavoring syrups.

These flavoring compositions can be optionally diluted with a polar solvent such as, for example, ethyl alcohol, ethyl acetate, propylene glycol, isopropyl alcohol and glycerin. The solvent functions as a carrier material which aids in incorporating the flavoring composition into a product. The diluent may optionally comprise one or more additional conventional components selected from the group consisting of colorants, lubricants, thickeners, emulsifiers, plasticizers and encapsulating agents such as gums, starches, dextrins and cyclodextrins.

Typically the flavoring composition will include 1–80% by weight of the succinate-based coolant compound and from 20–99% by weight of the flavorant diluent and optional polar solvent. More preferred flavorant compositions comprise 5–50% by weight of the succinate-based coolant compound and 50–95% by weight of the flavorant diluent and optional polar solvent.

The present invention also relates to a combination of a primary cooling agent selected from monomenthyl succinate, alkali metal salts of monomenthyl succinate, alkaline earth metal salts of monomenthyl succinate and mixtures thereof, with at least one secondary coolant component.

Secondary coolant components which may be used in combination with the primary coolant of the present invention include menthol, carboxamides, ketals, menthyl acetate, menthyl lactate, 3-menthoxypropane-1,2 diol and mixtures thereof. The carboxamide and ketal coolant compositions are known from the prior art and can be found, for example, in U.S. Pat. No. 5,009,893 and international patent application publication No. WO-93/23005, the disclosures of which are hereby incorporated by reference. The remaining secondary coolants are known cooling agents, some of which are commercially available.

More particularly, the carboxamide secondary coolants are selected from N-substituted-p-menthane-3-carboxamides of the formula:

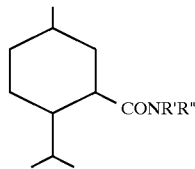

wherein R', when taken separately, is hydrogen or an aliphatic radical containing up to 25 carbon atoms; R" when taken separately is hydroxy or an aliphatic radical containing up to 25 carbon atoms, with the proviso that when R' is hydrogen R" may also be an aryl radical of up to 10 carbon atoms and selected from the group consisting of substituted phenyl, phenylalkyl, substituted phenylalkyl, naphthyl, substituted naphthyl and pyridyl; and R' and R", when taken together with the nitrogen atom to which they are attached, represent a cyclic or heterocylic group of up to 25 carbon atoms; acyclic tertiary and secondary carboxamides of the formula:

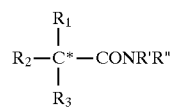

where R' and R", when taken separately, are each hydrogen, $C_1$–$C_5$ alkyl or $C_1$–$C_8$ hydroxyalkyl and provide a total of no more than 8 carbon atoms, with the proviso that when R' is hydrogen R" may also be alkylcarboxyalkyl of up to 6 carbon atoms; R' and R", when taken together, represent an alkylene group of up to 6 carbon atoms, the opposite ends of which group are attached to the amide nitrogen atom thereby to form a nitrogen heterocycle, the carbon chain of which may optionally be interrupted by oxygen; $R_1$ is hydrogen or $C_1$–$C_5$ alkyl; and $R_2$ and $R_3$ are each $C_1$–$C_5$ alkyl; with the provisos that (i) $R_1$, $R_2$, and $R_3$ together provide a total of at least 5 carbon atoms, preferably from 5–10 carbon atoms; and (ii) when $R_1$ is hydrogen, $R_2$ is $C_2$–$C_5$ alkyl and $R_3$ is $C_2$–$C_5$ alkyl and at least one of $R_2$ and $R_3$ is branched, preferably in an alpha or beta position relative to the carbon atom marked (*) in the formula; and mixtures thereof.

The ketal coolant compositions may be represented by the formula:

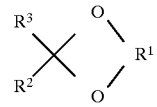

in which $R^1$ represents a $C_2$–$C_6$-alkylene radical having at least 1, but not more than 3, hydroxyl group(s), and either $R^2$ and $R^3$ independently of one another represent $C_1$–$C_{10}$-alkyl which is optionally substituted by 1 to 3 radicals selected from the group comprising hydroxyl, amino and halogen, $C_5$–$C_7$-cycloalkyl, preferably cyclohexyl, and $C_6$–$C_{12}$-aryl, preferably phenyl, with the proviso that the total of the C atoms of $R^1$ and $R^3$ is not less than 3, or $R^2$ and $R^3$ together represent an alkylene radical which, together with the carbon atom which carries the radicals $R^2$ and $R^3$, forms a 5–7 membered ring, optionally substituted by $C_1$–$C_6$-alkyl groups.

The relative amounts of the primary and secondary coolants in the composition of the present invention may be varied over a wide range of compositions depending upon the particular flavor desired. For example, when the strong minty taste of menthol is desirable, a combination of a large quantity of menthol with a relatively small quantity of the succinate-based coolant of the present invention may be desirable. Other potential combinations of the primary coolant with secondary coolant components will be apparent to the man of skill in the art.

Generally, the level of the secondary coolant compounds in the coolant composition of the present invention is from about 0.05% by weight to about 95% by weight, more preferably from about 0.1% by weight to about 70% by weight, and most preferably from about 0.5% by weight to about 50% by weight, based on the total weight of the composition. Typically, the coolant compositions are made by mixing the primary and secondary coolants together in a conventional manner.

Certain compositions of the present invention are illustrated by the following examples.

EXPERIMENTAL PROCEDURE FOR THE EXAMPLES

For each of the examples given below, a taste panel composed of 10–12 persons tasted the materials. The tasters were instructed to give information on the cooling effect, any unpleasant tastes and any other comments they might have. The following results were obtained from these tests.

EXAMPLE 1

Hard Candy

A hard candy formulation was made up from 120 grams of sugar, 30 grams of water, 80 grams of corn syrup and 0.1% by weight, based on the weight of the composition, of cinnamon flavor (control formulation). The formulation was divided into three parts. 0.05% by weight, based on the weight of the composition, of monomenthyl succinate was added to one of the hard candy formulations and 0.05% by weight, based on the weight of the composition of a commercially available coolant composition (WS3™) from Wilkinson-Sword) was added to the other hardy candy formulation for the purpose of comparison.

The taste panel found that the hard candy formulation containing the monomenthyl succinate provided a long-lasting, pleasant cooling effect whereas no cooling effect was present in the control. No minty flavor was noticed by the tasting panel. The hard candy formulation containing WS3™ also provided a cooling effect although the taste panel concluded that the cooling effect of WS3™ manifested itself in a different area of the mouth and throat than the cooling effect of the monomenthyl succinate of the invention.

EXAMPLE 2

Pressed Tablets

Royal T™ Dextrose (tabletting sugar) was pressed into two tablets, one containing only dextrose (control) and one containing 0.1% by weight of monomenthyl succinate. The taste panel noticed a pleasant cooling effect from the tablet containing the monomenthyl succinate and no cooling effect was obtained from the dextrose control tablet.

EXAMPLE 3

Mouthwash

Four samples of a mouthwash formulation having the following composition were tasted,

| | |
|---|---|
| cetyl pyridinium chloride | 0.757 grams |
| sodium saccharin | 1.75 grams |
| Tween ™ 80 | 0.5 fluid ozs. |
| D&C Green #5 (0.1% soln. in propylene glycol) | 0.8 fluid ozs. |
| D&C Yellow #10 (0.1 soln. in propylene glycol) | 0.2 fluid ozs. |
| Flavor N&A Mint Blend (0.2% soln.) | 0.25 fluid ozs. |
| Specially denatured alcohol | 31.0 fluid ozs. |

These ingredients were blended together until dissolved and then 96 fluid ozs. of water were added to provide a mouthwash formulation. The coolant compounds were then added to the mouthwash formulation in the amounts specified below.

The four mouthwash formulations tested were as follows: one containing no additives (control), one containing 0.004% by weight of monomenthyl succinate, one containing 0.004% by weight of WS3™ and one containing 0.002% by weight of monomenthyl succinate and 0.002% by weight of WS3™.

The taste panel noted a cooling effect in all three compositions although the taste panel concluded that each of the four mouthwash samples had a different taste and that the cooling effect of the monomenthyl succinate manifested itself in a different area of the mouth and throat than the cooling effect of WS3™ and the mouthwash. The cooling effects of the monomenthyl succinate, mouthwash mint flavor and WS3™ were found to be complementary in the fourth sample which contained all three coolants.

EXAMPLE 4

Mouthwash Containing Sodium Monomenthyl Succinate

The same four mouthwash formulations as were made in Example 3 were taste tested except that sodium monomenthyl succinate was substituted for the monomenthyl succinate in the same amounts. The tasting panel found a pleasant, long-lasting cooling sensation without bitterness for the sodium monomenthyl succinate-containing mouthwashes. The tasting panel also noted that the cooling sensation of sodium monomenthyl succinate was perceived at a point slightly forward of the point in the mouth and throat where the cooling sensation of monomenthyl succinate was perceived in the taste tests of Example 3. The sodium monomenthyl succinate was also found to have a complementary cooling effect when combined with $WS_3$™.

EXAMPLE 5

Carbonated Beverages

Four samples each of lemon-lime carbonated beverage were prepared, one without additives (control), one with 0.004% by weight of monomenthyl succinate, one with 0.004% by weight of WS3™ and one with 0.002% by weight of monomenthyl succinate and 0.002% by weight of WS3™. The carbonated beverage formulation was as follows, with all parts being parts by weight:

| | |
|---|---|
| High fructose corn syrup | 96.00 parts |
| Water | 28.90 parts |
| Sodium benzoate (25% solution w/w in water) | 0.50 parts |
| Citric acid (50% solution w/w in water) | 2.30 parts |
| Flavor N&A lemon-lime | 0.30 parts |

The carbonated beverage was formulated by combining the first three ingredients and mixing thoroughly, adding the citric acid solution and mixing again followed by adding the flavor to provide a beverage syrup. One part of the beverage syrup was then combined with 5 parts of carbonated water to provide the carbonated beverage. The coolant compounds were then mixed into the carbonated beverages om the amounts specified above.

The taste panel concluded that the samples containing monomenthyl succinate and WS3™ provided a cooling effect and that the cooling effect of monomenthyl succinate manifested itself in a different area of the mouth and throat than the cooling effect of WS3™. In addition, the cooling effect of monomenthyl succinate was found to be pleasing, not minty and long-lasting. Further, the combination of monomenthyl succinate with WS3™ was found to provide a complementary cooling effect since different areas of the mouth and throat were affected by the respective coolants.

EXAMPLES 6–8

Alcoholic Beverages

Three different alcoholic beverages were made by using 17.00 grams of high fructose corn syrup, 140.89 grams of water and 21.05, 42.11 and 84.22 grams of 190 proof alcohol in order to obtain alcoholic drinks of 20, 40 and 80 proof, respectively. To samples of each of the three alcoholic beverages was added 0.07% by weight of monomenthyl succinate. A cooling effect was noted in the 20 and 40 proof alcoholic beverages containing the monomenthyl succinate but not in the 80 proof beverage.

As a result, a new sample of 80 proof alcoholic beverage was prepared using a higher concentration of monomenthyl succinate and, at this higher concentration level a pleasant, long-lasting cooling effect was noticed by the tasting panel. In addition, the tasting panel concluded that the monomenthyl succinate enhanced the taste sensation of the alcohol in all of the alcoholic beverages and, as a result, the 20, 40 and 80 proof alcoholic beverages including monomenthyl succinate each tasted as if there were a higher alcohol content than the corresponding control beverage having the same alcohol content no coolant compound.

EXAMPLE 9

Chewing Gum

A conventional chewing gum base was employed for this example. To the chewing gum base was added 1.0% by weight of mixed berry flavoring. Then, to one of the chewing gum samples 0.30% by weight of monomenthyl succinate was added. A pleasant, long-lasting cooling effect in the back of the mouth and throat was noted by the tasting panel in the chewing gum containing monomenthyl succinate. In addition, no minty taste was apparent.

EXAMPLE 10

Sugarless Candy

Sugarless deposited sorbitol candy was prepared by heating one kilogram of sorbitol syrup to 170° C., cooling the sorbitol syrup to 135° C., adding 12 grams of citric acid with stirring and cooling this composition down to 110° C. At that point, 20 grams of sorbitol powder and the flavorant including 0.05% by weight, based on the weight of the composition of monomenthyl succinate was added to the sugarless candy formulation by stirring it in slowly. Finally, the candy is deposited and allowed to harden.

A taste panel found that the sugarless hard candy formulation containing the monomenthyl succinate provided a long-lasting pleasant cooling effect.

These examples have been given for the purpose of illustration and description only and are not to be construed as limiting the scope of the invention in any way. The scope of the invention is to be determined from the claims appended hereto.

What is claimed is:

1. A composition selected from topical products for humans and animals, oral care products, nasal care products, and chewing gum which comprises a product base and an effective amount of a coolant selected from the group consisting of monomenthyl succinate, alkali metal salts of monomenthyl succinate, alkaline earth metal salts of monomenthyl succinate and mixtures thereof.

2. A composition as claimed in claim 1 which comprises from 0.001–1.0% by weight, based on the total weight of the composition, of said coolant.

3. An ingestible product for humans or animals which comprises a product base selected from the group consisting of baked goods, dairy products, fruit ices, confectionery products, sugarless candies, jams, jellies, gelatins, puddings, animal feeds, pressed confectionery tablets, hard-boiled candies, pectin-based candies, chewy candies, creme-centered candies, fondants, sugarless hard-boiled candies, sugarless pectin-based candies, sugarless chewy candies, sugarless creme-centered candies, toothpastes, mouthwashes, breath fresheners, carbonated beverages, mineral waters, powdered beverage mixes, other non-alcoholic beverages, cough drops, lozenges, cough mixtures, decongestants, anti-irritants, antacids, anti-indigestion preparations and oral analgesics, and an effective amount of a coolant selected from the group consisting of monomenthyl succinate, alkali metal salts of monomenthyl succinate, alkaline earth metal salts of monomenthyl succinate and mixtures thereof.

4. A composition as claimed in claim 3 wherein the orally ingested products are selected from lozenges, cough mixtures, decongestants, anti-irritants, antacids, anti-indigestion preparations and oral analgesics.

5. A coolant composition which comprises an effective amount of at least one primary coolant selected from the group consisting of monomenthyl succinate, alkali metal salts of monomenthyl succinate and alkaline earth metal salts of monomenthyl succinate, and at least one secondary coolant component selected from the group consisting of carboxamides, ketals, menthyl acetate, menthyl lactate, 3-menthoxypropane-1,2 diol and mixtures thereof.

6. A composition as claimed in claim 3 wherein the ingestible product is a foodstuff selected from the group consisting of baked goods, dairy products, fruit ices, confectionery products, sugarless candies, jams, jellies, gelatins, puddings and animal feeds.

7. A composition as claimed in claim 3 wherein the topical product is selected from the group consisting of face creams, talcum powders, hair oils, shampoos, bath oils, bath salts, toilet soaps, colognes, antiperspirants, toilet water, perfume, shaving lotion, shaving cream, hair tonic, ointments and lotions.

8. A composition as claimed in claim 3 wherein the oral care product is selected from dentifrices and mouthwashes.

9. A composition as claimed in claim 3 wherein the ingestible product is cough drops.

10. A composition as claimed in claim 3 which comprises from 0.001–1.0% by weight, based on the total weight of the composition, of said coolant.

11. A composition as claimed in claim 3 wherein the coolant is selected from the group consisting of monomenthyl succinate and the sodium salt of monomenthyl succinate.

12. A composition as claimed in claim 3 wherein said composition is selected from pressed confectionery tablets, hard boiled candies, pectin-based candies, chewy candies, cream-centered candies, fondants, sugarless hard-boiled candies, sugarless pectin-based candies, sugarless chewy candies, sugarless cream-centered candies, animal feeds, breath fresheners, carbonated beverages, mineral waters, powdered beverage mixes and non-alcoholic beverages.

13. An end use composition selected from topical products for humans or animals, oral care products, nasal care products, and chewing gum, which comprises a product base and an effective amount of a coolant composition as claimed in claim 5.

14. A coolant composition as claimed in claim 5 wherein the carboxamide coolant component is selected from the group consisting of:

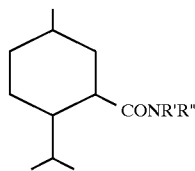

where R', when taken separately, is hydrogen or an aliphatic radical containing up to 25 carbon atoms; R" when taken separately is hydroxy, or an aliphatic radical containing up to 25 carbon atoms, with the proviso that when R' is hydrogen R" may also be an aryl radical of up to 10 carbon atoms and selected from the group consisting of phenyl, phenalkyl, naphthyl, and pyridyl; and R' and R", when taken together with the nitrogen atom to which they are attached, represent a cyclic or heterocylic group of up to 25 carbon atoms;

acyclic tertiary and secondary carboxamides of the formula:

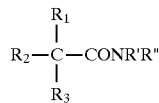

where R' and R", when taken separately, are each hydrogen, $C_1$–$C_5$ alkyl or $C_1$–$C_8$ hydroxyalkyl and provide a total of no more than 8 carbon atoms, with the proviso that when R' is hydrogen R" may also be alkylcarboxyalkyl of up to 6 carbon atoms; R' and R", when taken together, represent an alkylene group of up to 6 carbon atoms, the opposite ends of which group are attached to the amide nitrogen atom thereby to form a nitrogen heterocycle, the carbon chain of which may optionally be interrupted by oxygen; $R_1$ is hydrogen or $C_1$–$C_5$ alkyl; and $R_2$ and $R_3$ are each $C_1$–$C_5$ alkyl; with the provisos that (i) $R_1$, $R_2$, and $R_3$ together provide a total of at least 5 carbon atoms; and (ii) when $R_1$ is hydrogen, $R_2$ is $C_2$–$C_5$ alkyl and $R_3$ is $C_2$–$C_5$ alkyl and at least one of $R_2$ and $R_3$ is branched and mixtures thereof.

15. A coolant composition as claimed in claim 5 wherein the ketal coolant component is selected from the group consisting of:

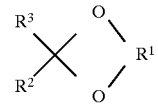

in which $R^1$ represents a $C_2$–$C_6$-alkylene radical having at least 1, but not more than 3, hydroxyl group(s), and either $R^2$ and $R^3$ independently of one another represent $C_1$–$C_{10}$-alkyl which is optionally substituted by 1 to 3 radicals selected from the group consisting of hydroxyl, amino, halogen, $C_5$–$C_7$-cycloalkyl, $C_6$–$C_{12}$-aryl, with the proviso that the total of the C atoms of $R^2$ and $R^3$ is not less than 3, or $R^2$ and $R^3$ together represent an alkylene radical which, together with the carbon atom which carries the radicals $R^2$ and $R^3$, forms a 5–7 membered ring, optionally substituted by $C_1$–$C_6$-alkyl groups.

16. A coolant composition as claimed in claim 5 wherein the primary coolant is selected from the group consisting of monomenthyl succinate and monomenthyl sodium succinate.

17. An end use composition as claimed in claim 13 which comprises from 0.001–1.0% by weight, based on the total weight of the composition, of said primary coolant.

18. A end use composition as claimed in claim 17 wherein the primary coolant is selected from monomenthyl succinate and monomenthyl sodium succinate.

* * * * *

(12) EX PARTE REEXAMINATION CERTIFICATE (7686th)
United States Patent
Mane et al.

(10) Number: US 5,843,466 C1
(45) Certificate Issued: Aug. 17, 2010

(54) COOLANT COMPOSITIONS

(75) Inventors: Jean M. Mane, Grasse (FR); Jean-Louis Ponge, Grasse (FR)

(73) Assignee: V. Mane Fils S.A., Le Bar sur Loup (FR)

Reexamination Request:
No. 90/009,476, Jun. 15, 2009

Reexamination Certificate for:
Patent No.: 5,843,466
Issued: Dec. 1, 1998
Appl. No.: 08/629,598
Filed: Apr. 9, 1996

Related U.S. Application Data

(63) Continuation-in-part of application No. 08/520,399, filed on Aug. 29, 1995, now Pat. No. 5,725,865.

(51) Int. Cl.
*A24D 3/14* (2006.01)
*A24D 3/00* (2006.01)
*A23G 3/00* (2006.01)
*A23G 4/00* (2006.01)
*A23L 1/226* (2006.01)

(52) U.S. Cl. ............... 424/401; 424/48; 424/49; 424/55; 424/65; 424/69; 424/70.1; 424/73; 424/400; 424/439; 424/440; 424/441; 424/442; 424/464; 424/489; 426/534; 426/549; 426/580; 426/590; 514/774; 514/777; 514/819; 514/844; 514/849; 514/853; 514/887

(58) Field of Classification Search .................. None
See application file for complete search history.

(56) References Cited

U.S. PATENT DOCUMENTS 3,111,127 A 11/1963 Jarboe et al.
3,136,319 A 6/1964 Jarboe et al.
3,793,446 A 2/1974 Moeller et al.
3,917,613 A 11/1975 Humbert et al.
4,033,994 A 7/1977 Watson et al.
5,009,893 A 4/1991 Cherukuri et al.

FOREIGN PATENT DOCUMENTS

GB 1 353 381 5/1974
WO WO 93/23005 11/1993

OTHER PUBLICATIONS

"A Survey of Pysically Active Organic Infusoricidal Compounds and Their Soluble Derivatives With Special Reference to Their Action on the Rumen Microbial System," Eadle, J.M. et al., J. Gen. Microbiol., (1956), 14, 122–133.

"A Molecular Approach to Flavor Synthesis. I. Menthol Esters of Varying Size and Polarity," H. Jabloner et al., Journal of Polymer Science, Polymer Chemistry Edition (1980), vol. 18, 2933–2940.

*Primary Examiner*—Gary L Kunz

(57) ABSTRACT

Coolant compositions, flavorant compositions and ingestible and topical compositions containing at least one coolant compound selected from monomenthyl succinate, alkali metal salts of monomenthyl succinate, alkaline earth metal salts of monomenthyl succinate and mixtures thereof. These compositions are found to provide a pleasant, long-lasting cooling effect without bitterness and the cooling effect manifests itself differently than the cooling effect of other known coolants. As a result, a complementary or synergistic effect can by obtained by combination with other coolants. Further, the succinate-based coolant compounds of the invention are found to enhance the sensation of alcohol in alcoholic beverages.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-18 is confirmed.

* * * * *